(12) United States Patent
Zhang et al.

(10) Patent No.: US 6,370,434 B1
(45) Date of Patent: Apr. 9, 2002

(54) CARDIAC LEAD AND METHOD FOR LEAD IMPLANTATION

(75) Inventors: Yongxing Zhang, Little Canada; James O. Gilkerson, Stillwater, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/514,544

(22) Filed: Feb. 28, 2000

(51) Int. Cl.$^7$ .................................................. A61N 1/05

(52) U.S. Cl. ....................................................... 607/122

(58) Field of Search ................................. 607/121, 122

(56) References Cited

U.S. PATENT DOCUMENTS

| | | | |
|---|---|---|---|
| 5,383,922 A | * | 1/1995 | Zipes et al. |
| 5,755,766 A | | 5/1998 | Chastain et al. ............. 607/122 |
| 5,803,928 A | | 9/1998 | Tockman et al. ............ 607/122 |
| 5,876,431 A | | 3/1999 | Spehr et al. ................. 607/126 |

* cited by examiner

Primary Examiner—Scott M. Getzow
(74) Attorney, Agent, or Firm—Nikolai & Mersereau, P.A.

(57) ABSTRACT

A pacing lead and method for implanting the lead are provided. The lead includes a reduced diameter lead body and an electrode assembly. The electrode assembly is provided with a stylet guide, a cavity or a flange to facilitate the leads implantation with the reduced diameter lead body. The method for implanting further includes providing a guide catheter and a stylet to locate the electrode assembly at a target position in the heart.

14 Claims, 4 Drawing Sheets

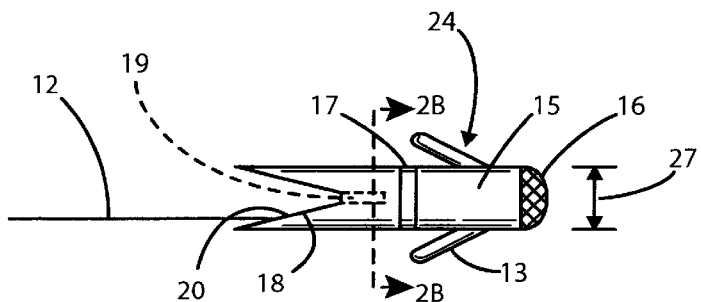 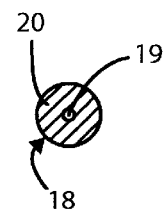
FIG. 2A FIG. 2B
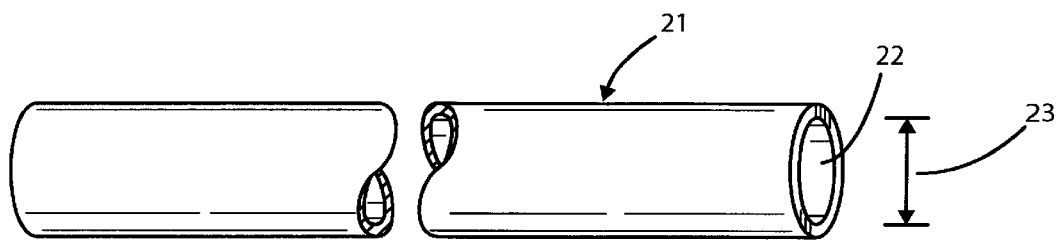
FIG. 2C
FIG. 2D

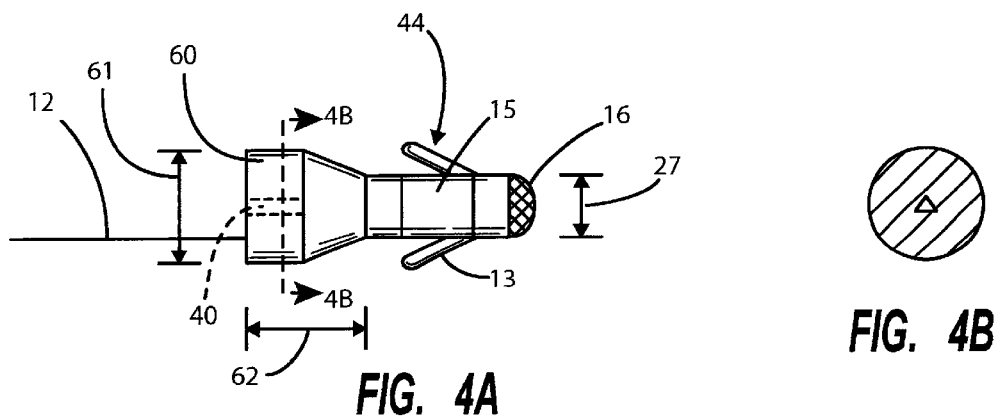
FIG. 4A
FIG. 4B
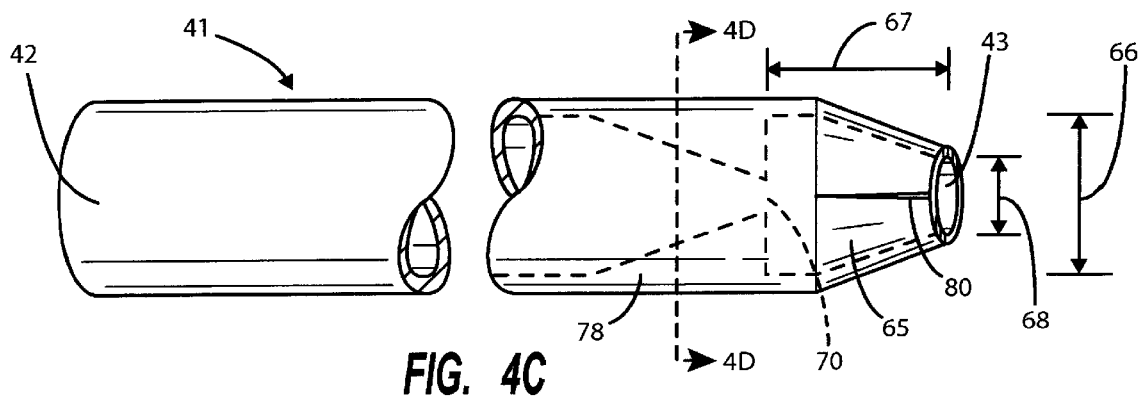
FIG. 4C
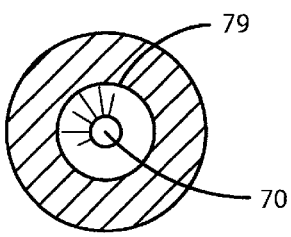
FIG. 4D
FIG. 4E

CARDIAC LEAD AND METHOD FOR LEAD IMPLANTATION

FIELD OF THE INVENTION

The present invention relates generally to cardiac stimulation leads, and more particularly to an implantable cardiac leads including an electrode and a reduced diameter lead body.

BACKGROUND OF THE INVENTION

Implantable leads form an electrical connection between a pulse generator or other electronic device and a tissue or structure in the body. For example, leads transmit electric signals used to stimulate cardiac or nerve tissue in one direction and signals generated by sensors placed in proximity to particular organs or tissues in the opposite direction. Leads typically include one or more electric elements at the lead's distal end. The electric elements are designed to form an electrical connection with a tissue or organ. Most leads also include a lead connector pin at the lead's proximal end. Lead connector pins are adapted to electrically and mechanically connect leads to the pulse generators or other electronic medical devices. A flexible conductor connects the electric element to the lead connector pin. Commonly, the flexible conductor takes the form of a single or multifilar wire coil, although, there is an increasing interest in using stranded cables as conductors. Regardless of the form, a layer of insulating material typically surrounds the flexible conductors. Together, the flexible conductor and the insulating layer form the lead body. The lead body couples the lead connector pin at its proximal end with the electric element at its distal end.

Leads are implanted in the cardiovascular system, typically through a vein, to confer a stimulus to a specific location within the heart. The introduction of a lead into the vein and heart necessarily at least partially obstructs blood flow. In addition, the diameter of the lead can reduce the efficiency of valve function in the heart and veins. Blood flow and valve obstruction problems increase when a patient's treatment requires the implantation of multiple leads. The placement of a conventional, prior art pacing lead in individuals suffering from ischemia can further exacerbate the individual's problems. Thus, despite the many advantages associated with endocardial leads, there has always been a tradeoff associated with their use in many patients.

The degree of blood vessel obstruction is a function of a lead body's diameter. Thus, reducing lead body diameter will reduce the degree of obstruction. This can be extremely important with children. Children are inherently more susceptible to having blood flow obstructed because many of their blood vessels are simply too small to accommodate conventional implantable leads. Further complicating their situation, children are often the least able to adjust to a diminished blood flow or impaired valve function. In a similar fashion, adult patients with occluded vessels or impaired valves are also susceptible to having their blood flow obstructed. These adult patients may not be suitable candidates for transvenous implanted leads because of the diameter of currently available leads. Thus, a need exists for a reduced diameter lead body to minimize the obstruction to blood flow from intravenously implanted leads.

Conventional lead designs have several disadvantages. Typical methods for lead implantation require that the lead body receive a stylet. Conventional lead bodies have an internal lumen that is coextensive with the lead body to accommodate the stylet. The stylet enables the lead to be steered within the vessels to a target location in the heart. This internal lumen adds to the lead's diameter. The lumen's diameter often constitutes a significant portion of the overall diameter of the lead body. Similarly, conventional lead bodies often incorporate coiled conductor wires. The coiling necessarily doubles the wires diameter and typically creates a central lumen along the coil's axis. For the above reasons, the smallest available conventional leads may still be too large for successful transvenous implantation in some patients. Thus, a need exists for a method for implanting a lead having a reduced size lead body.

In addition, when multiple conventional leads are introduced into a patient there is a tendency for the leads to abrade one another and the tissue of the patient due to the rigidity of the lead bodies. The inter-lead abrasion reduces the life of the lead and increases the frequency of surgery to replace the worn leads. The lead body to tissue abrasion can traumatize the tissues of the circulatory system. Thus, a need exists for a lead having better flexibility to reduce the effects of abrasion. Finally, conventional tissue stimulating leads also require a relatively large amount of raw material for their manufacture. This increases production costs. Thus, a need exists for a lead requiring less raw material for manufacture.

SUMMARY OF THE INVENTION

The present invention meets the above needs and provides additional advantages and improvements that will be evident to those skilled in the art. The present invention provides an improved lead having a reduced diameter lead body and a method for implanting the lead within the heart.

In a first aspect of the invention, the lead includes an electrode assembly having a stylet guide and a reduced diameter lead body. The reduced diameter lead body electrically is coupled to the electrode assembly. The electrode assembly defines the stylet guide that is configured to guide a stylet into a position at a proximal end of the electrode assembly during implantation. The stylet guide may include a conical surface. The stylet guide enables the electrode assembly to be easily pushed through a guide catheter. The stylet guide eliminates the need to have a lead body capable of receiving a stylet and hence allows for the reduced diameter lead body. The distal end of the electrode assembly can include a cavity configured to removably secure a distal end of a pushing stylet. Including such a cavity enables the pushing stylet to be better maintained on the electrode assembly during implantation. The reduced diameter lead body may include a cable or coil conductor and an insulator. The electrode assembly may be of a passive fixation or an active fixation design. If the electrode assembly uses passive fixation, the assembly may include at least one tine to fix the electrode at a target location. If the electrode assembly uses active fixation, the assembly may include a screw helix as is known in the art.

The method for implanting a lead conforming to the first aspect of the present invention includes a guide catheter and a pushing stylet. The distal end of the guide catheter is positioned at a target location within the heart of a patient. The guide catheter may include a radio-opaque coating allowing the catheter to be visualized during positioning using fluoroscopy, magnetic resonance imaging, echocardiography, or by other methods known to those skilled in the art. The electrode assembly is placed within the guide catheter's lumen at the proximal end of the guide catheter. The stylet guide is oriented to receive the distal end of the pushing stylet. The pushing stylet is passed through the proximal end of the guide catheter. In doing so, the distal end of the pushing stylet abuts the proximal end of the electrode assembly and thereby pushes the electrode assembly through the catheter to the target location in the patient's heart. Once the electrode assembly is at the target location, it is secured to the target location. Once secured the pushing stylet and catheter are withdrawn from the heart.

In a second aspect of the invention, the lead includes an electrode assembly having a cavity and a reduced diameter lead body. The cavity is configured to frictionally engage a distal end of a pushing stylet. This configuration allows the electrode assembly to be guided through a catheter to a target location with the pushing stylet. Thus, the cavity eliminates the need to have a lead body having a lumen extending the length thereof and capable of receiving a stylet for implantation. This allows a reduced diameter lead to be used. The reduced diameter lead body is electrically coupled to the electrode assembly. The reduced diameter lead body may include a cable or coil conductor and an insulator covering same. The electrode assembly may be of a passive fixation or an active fixation design. If the electrode assembly uses passive fixation, the assembly may include at least one tine to fix the electrode at a target location. If the electrode assembly uses active fixation, the assembly may include a screw helix.

The method for implanting a lead conforming to the second aspect of the present invention also includes a guide catheter and a pushing stylet. The distal end of the guide catheter is positioned at a target location within the heart of a patient. The guide catheter may include a radio-opaque coating or marker bands allowing the catheter to be visualized during positioning using fluoroscopy, magnetic resonance imaging, echocardiography, or by other methods known to those skilled in the art. The distal end of the pushing stylet is inserted into the cavity at the proximal end of an electrode assembly. This frictionally secures the electrode assembly to the pushing stylet. The pushing stylet and electrode assembly are then inserted through the proximal end of the guide catheter and advanced through the catheter to the target location at the catheter's distal end by pushing on the stylet. The catheter is brought into contact with the target location and is secured to the location.

The pushing stylet is then removed from the electrode assembly's cavity. The pushing stylet may be removed from the electrode using a removal catheter. The removal catheter is inserted through the proximal end of the guide catheter. The removal catheter is passed through the guide catheter until the distal end of the removal catheter abuts the proximal end of the electrode. A stabilizing force is applied to the distal end of the electrode assembly by the removal catheter allowing the user to dislodge the pushing stylet from the cavity without displacing the electrode assembly. The pushing stylet, the guide catheter and the removal catheter are then removed from the patient.

In a third aspect of the invention, the lead includes an electrode assembly having a flange at its proximal end and a reduced diameter lead body. The flange is configured to be secured within the distal end of a guide catheter. The guide catheter's distal end may include a receiving cavity adapted to receive the flange. Securing the electrode in the catheter's distal end allows the guide catheter to transport the electrode assembly to a target location in the heart without use of a stylet wire. The reduced diameter lead body is electrically coupled to the electrode assembly. The reduced diameter lead body may include a cable or coil conductor and a cover insulator. The electrode assembly may be of a passive fixation or an active fixation design. If the electrode assembly uses passive fixation, the assembly may include at least one tine to fix the electrode at a target location. If the electrode assembly uses active fixation, the assembly may include a screw helix.

The method for implanting a lead conforming to the third aspect of the present invention includes a guide catheter and a removal stylet. The flange of the electrode assembly is secured to the distal end of the catheter. The distal end of the guide catheter and the electrode assembly are advanced through a blood vessel with the electrode assembly being positioned at a target location within the heart of a patient.

The guide catheter can be of the peel-away variety or may take other forms that will be recognized by those skilled in the art. It may also include a radio-opaque coating, allowing the catheter to be visualized during positioning using fluoroscopy, magnetic resonance imaging, echocardiography, or by other methods known to those skilled in the art. The electrode assembly is secured at the target location. Either prior to or after the electrode assembly is secured, a removal stylet is then inserted into the proximal end of the guide catheter and passed through the guide catheter until its distal end comes into contact with the proximal end of the electrode assembly. The removal stylet can be used to apply a force to the distal end of the electrode assembly to simply detach the flange on the electrode assembly from the guide catheter or it can additionally cooperate with a cavity in the proximal end of the electrode assembly to actively fix the electrode. Alternatively, the electrode assembly of a type having a corkscrew tip is secured to the target location by rotating a proximal end of the guide catheter prior to detaching the electrode assembly from the distal end of the guide catheter. After the electrode assembly is secured and the electrode assembly is removed, the catheter and the removal stylet are withdrawn from the patient.

In addition, upon review of the following disclosure, those skilled in the art will recognize additional aspects, advantages and improvements conferred by the present invention.

BRIEF DESCRIPTION OF THE DRAWINGS

FIG. 2A illustrates a side view of an embodiment of the reduced diameter lead's electrode assembly;

FIG. 2B illustrates a sectional view taken along line 2b—2b in the electrode assembly of FIG. 2A;

FIG. 2C illustrates a partial isometric view of an embodiment of a guide catheter for use during the implantation of the electrode assembly of FIG. 2A;

FIG. 2D illustrates a partial side view of an embodiment of a stylet for use during the implantation of the electrode assembly of FIG. 2A;

FIG. 4A illustrates a fragmentary side view of a further embodiment of the reduced diameter lead and electrode assembly;

FIG. 4B illustrates a sectional view taken along line 4b—4b of the electrode assembly of FIG. 4A;

FIG. 4C illustrates a partial isometric view of an embodiment of a guide catheter for use during the implantation of the electrode assembly of FIG. 4A;

FIG. 4D illustrates a sectional view taken along line 4d—4d of the guide catheter of FIG. 4C; and FIG. 4E illustrates a partial side view of a stylet for use during the implantation of the electrode assembly of FIG. 4A;

DETAILED DESCRIPTION OF THE INVENTION

Figure 1:
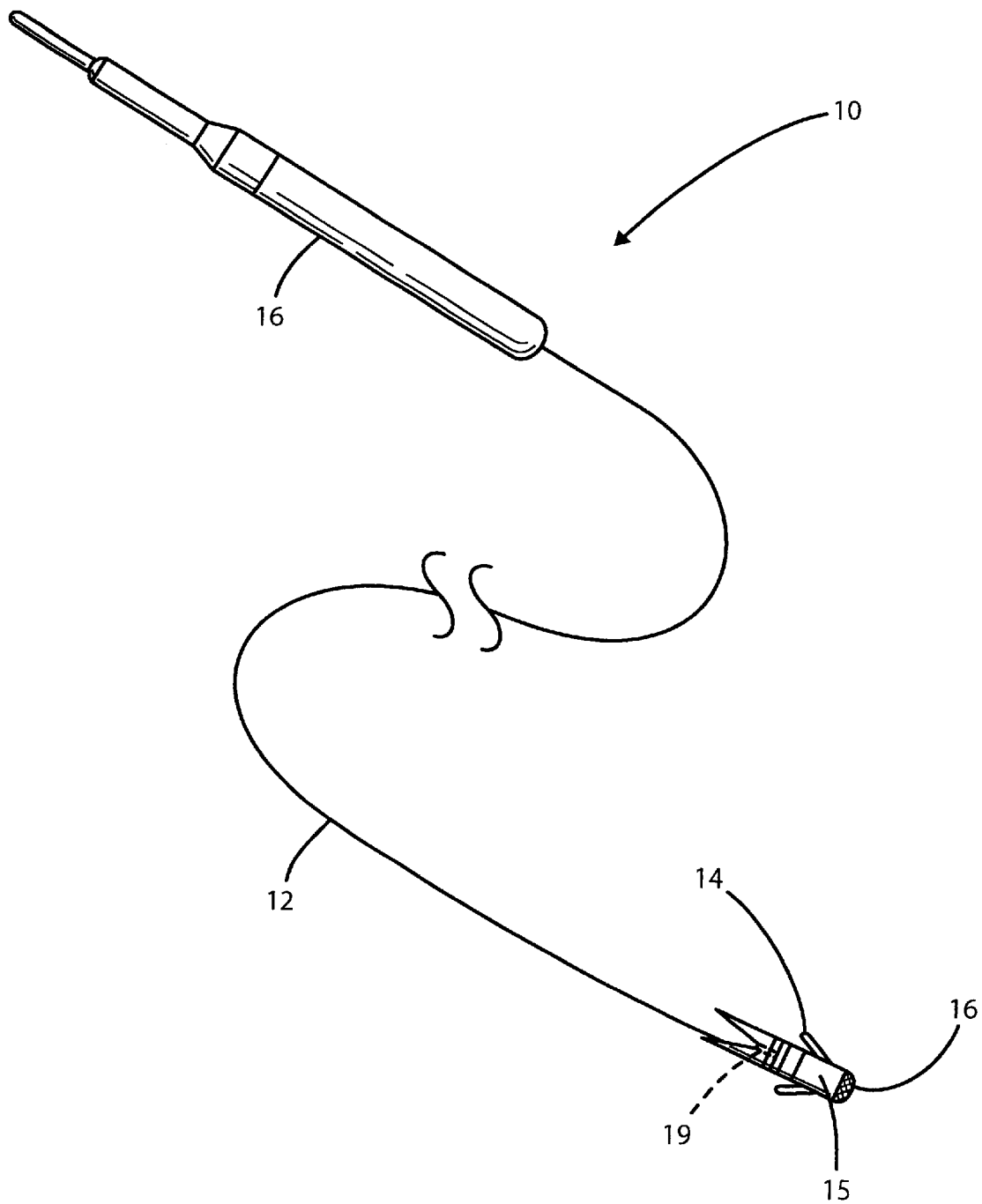
FIG. 1 illustrates a plan view of an embodiment of a reduced diameter lead for cardiac pacing.

The present invention is applicable to a variety of implantable medical devices for providing an electric current to selected body tissues or transmitting signals from a sensing electrode to the medical device. The invention is described in the context of an electrode on a cardiac lead and a method for implanting the lead into the right atrium or right ventricle as a specific example for illustrative purposes only. The appended claims are not intended to be limited to any specific example or embodiment described in this patent. It will be understood by those skilled in the art that the present invention may be used to implant a wide variety of leads including, but not limited to, sensing/pacing leads, unipolar leads, multipolar leads, and leads with extendable screw helix positive fixation electrodes. Further, in the drawings described below, the reference numerals are generally repeated where identical elements appear in more than one figure.

FIG. 1 illustrates a lead 10 made in accordance with the present invention. Lead 10 includes a reduced diameter lead body 12, a pacing electrode assembly 14 and a lead connector pin 16. Lead 10 is generally configured to transmit an electric signal from a pulse generator (not shown) to an implanted electrode to confer an electrical stimulus on the heart. The pulse generator may be a cardiac rhythm management device, such as a pacemaker, a cardioverter/defibrillator, or a sensing/diagnostic instrument. Lead connector pin 16 is provided at the proximal end of lead body 12. Lead connector pin 16 is configured to form an electrical connection with the cardiac rhythm management device in a well-known manner. Typically, the lead connector pin conforms to the international standard IS-1 when used to connect a lead to a pacemaker, although, it could take any number of forms known to those skilled in the art. Lead connector pin 16 may be electrically coupled to the lead body by crimping, spot welding, laser welding, electrically conductive adhesives or by other means known to those skilled in the art.

Pacing electrode assembly 14 is provided at the distal end of lead body 12. To stimulate the heart, pacing electrode assembly 14 can be positioned within the right atrium or right ventricle adjacent or within the heart tissue. Pacing electrode assembly 14 includes a cylindrical housing 15 and at least one electrode, shown for exemplary purposes as tip electrode 16 and ring electrode 17. The housing 15 is typically configured to allow the pacing electrode assembly 14 to be secured in or on the heart. The electrodes are typically composed of a biocompatible conducting material, such as stainless steel, MP35N or other electrically conductive pacing electrode materials known to those skilled in the art. The electric elements may take a number of forms such as tip electrodes, ring electrodes, split ring electrodes or bar electrodes recognized by those skilled in the art.

In addition, electrode assemblies are typically provided with a structure to fix the electrode to the target tissue. The fixation structures fall into two general categories: passive fixation and active fixation. Passive fixation structures secure electrode assemblies to a target tissue by intertwining with a structure in the heart. Typically with pacing leads, passive fixation is accomplished by the use of tines 13 (shown in FIGS. 2A, 3A and 4A) that interlock with the trabeculae in the right ventricle of the heart. Active fixation structures secure electrode assemblies to a target tissue by invasively securing the electrode assembly or a part thereof within the tissue. Typically with pacing leads, active fixation is accomplished with a screw helix (not shown) positioned on the distal end of the electrode assembly. The screw helix requires the user apply a torque to screw the helix into the target tissue. The configurations of electrode assemblies and their components are diverse and the application of the various configurations to the present invention will be evident to one skilled in the art.

Reduced diameter lead body 12 includes an insulator surrounding one or more conductors. Lead body 12 typically does not include a lumen for the insertion of a stylet. This enables lead body 12 to have a reduced diameter when compared with typical lead bodies. The lead body typically includes at least one conductor and a surrounding insulator. The insulator functions to electrically isolate the filars comprising the conductor from body fluids and tissues. To a lesser extent, the insulator can function to mechanically secure lead body 12 to lead connector pin 16 and to pacing electrode assembly 14. Therefore, the insulator is substantially coextensive with the conductor. The insulator may be made from a variety of materials including silicone, polyurethane, polyethylene, polyimide, PTFE, ETFE, or other materials known to those skilled in the art. Insulators are generally designed to provide biocompatible electrical insulation for the conductor while presenting a smooth external surface.

Typically, the conductor is in the form of a cable or a coil. The cable may be a single filar or may include a plurality of filars depending upon the requirements for the specific application. The coil conductor may also be used but typically will be wound using a single or multiple filars such that there is only a small lumen or no lumen at all to reduce the overall diameter. The presence of a lumen would allow the delivery of drugs to the treated tissue. The filars are typically composed of stainless steel, MP35N, drawn-brazed-strand (DBS) or other conductive materials known to those skilled in the art. The lead body's diameter, including insulator and conductor, is typically smaller than 1.56 millimeters and may be as small as 0.22 millimeter, although the lead body's diameter may even be further reduced if the conductor material, insulator material and/or specific application permit. Regardless of the conductor used, the lead should be capable of readily conforming to the irregular passageways and shapes of the cardiovascular system. Accordingly, the lead body should have enough flexibility to permit the lead body to flex easily, and elastically.

FIGS. 2A–D illustrate a further embodiment of the present invention, including a pacing electrode assembly and an apparatus for implanting the electrode assembly. FIG. 2A shows a bipolar electrode assembly 24 having an electrode housing 15, a tip electrode 16, a ring electrode 17 and a reduced diameter lead body 12. In the bipolar configuration shown in FIG. 2A, tip electrode 16 and ring electrode 17 are individually electrically coupled to a first conductor and a second conductor, respectively, at the distal end lead body 12. A lead connector pin (not shown) is typically electrically coupled to the first and second conductors at the proximal end of lead body 12. The electrical elements and lead connector pin may be electrically coupled to the lead body by crimping, spot welding, laser welding, electrically conductive adhesives or by other means known to those skilled in the art. In the embodiment shown, tip electrode 16 and ring electrode 17 are configured within the electrode housing 15 to confer a pacing stimulus on the heart.

Pacing electrode assembly 24 (as shown in FIG. 2A) is generally configured for advancing through a guide catheter 21 (shown in FIG. 2C) to the right atrium or the right ventricle. To facilitate advancing through a guide catheter 21, electrode assembly 14 is configured to have a smaller outside diameter 27 than the inside diameter 23 of lumen 22. Further, electrode assembly 24 is provided with a stylet guide 18 and a cavity 19 at its proximal end. Stylet guide 18 is configured to guide a distal tip 26 (shown in FIG. 2D) of a pushing stylet 25 into cavity 19. Stylet guide 18 is typically integral with the electrode housing. In the embodiment shown in FIGS. 2A–B, stylet guide 18 presents a conical surface 20. Conical surface 20 on stylet guide 18 is configured to contact the advancing distal tip 26 and to guide distal tip 26 into cavity 19. Thus, when electrode assembly 24 is within a lumen 22 of guide catheter 21, distal tip 26 of pushing stylet 25 can be directed first by guide catheter 21 and then by stylet guide 20 into cavity 19 simply by advancing pushing stylet 25 through lumen 22 of guide catheter 21.

Guide catheter 21 may of the peel-away variety or take other forms recognized by those skilled in the art. Guide catheter 21 is typically constructed of a biocompatible flexible material. Guide catheter 21 can include radio-opaque marker bands, a radio-opaque coating or a radio-opaque component in its composition to facilitate visualization with fluoroscopy, magnetic resonance imaging, echocardiography, or by other methods known to those skilled in the art during implantation.

Cavity 19 is configured to releasably secure distal tip 26 such that after electrode assembly 24 has been positioned, with passive fixation, at the target location the stylet's distal tip 26 can be withdrawn from the cavity without dislodging the electrode or significantly damaging the heart. Alternatively, for active fixation, cavity 19 is configured to releasably secure and cooperate with the shape of distal tip 26 such that after electrode assembly 24 has been positioned at the target location distal tip 26 can confer a rotational force to fix a screw helix into the target location.

Pushing stylet 25 is typically a biocompatible metal wire configured to push electrode assembly 24 through lumen 22 of guide catheter 21. Pushing stylet 25 should be rigid enough to overcome the frictional and hydrostatic forces encountered as the electrode advances through guide catheter 21 to the target location in the heart. Distal tip 26 of pushing stylet 25 is typically cylindrical along its longitudinal axis, although, as mentioned above, when cooperating with cavity 19 to actively fix an electrode, the shape will be such that a force can be conferred to electrode apparatus 24. Typically, the shape will be non-circular, like for example rectangular, triangular, square or any number of shapes known to those skilled in the art. Similarly, cavity 19 is typically circular to receive distal tip 26, although its shape will cooperate with distal tip 26 when required for active fixation.

A method for implanting electrode assembly 24 is best understood with reference to FIGS. 2A–D. The method is described in the context of inserting an electrode into the right ventricle for exemplary purposes only. The distal end of guide catheter 21 is inserted into a vein of a patient using the Seldinger technique or other venipuncture techniques known to those skilled in the art. The distal end is guided through the veins and right atrium into the right ventricle and the tip is positioned adjacent the target location. Typically, the distal end is guided to the target location with the assistance of a fluoroscopy, magnetic resonance imaging, echocardiography, or by other methods known to those skilled in the art. Once positioned adjacent the target location, the distal end is held in position. Electrode assembly 24 is then inserted into lumen 22 at the proximal end of guide catheter 21. Distal tip 26 of pushing stylet 25 is then inserted into lumen 22. Pushing stylet 25 is advanced toward the distal end of guide catheter 22 and, in doing so, distal tip 26 is directed into cavity 19 by conical surface 20 of stylet guide 18 acting like a funnel. Pushing stylet 25 is advanced and thereby, pushes electrode assembly 24 through the catheter. Frictional forces acting on electrode assembly 24 oppose the pushing force from pushing stylet 25 to maintain distal end 26 within cavity 19. To a lesser degree, frictional forces within the cavity can contribute to maintaining distal end 26 within cavity 19, but the frictional force is typically not sufficient to prevent the withdrawal of distal end 26 from cavity 19.

Upon reaching the target location, if the electrode assembly uses passive fixation, the tines are entangled in the trabeculae of the right ventricle and distal tip 26 of pushing stylet 25 is withdrawn from cavity 19. If electrode assembly 24 uses active fixation, the proximal end of pushing stylet 25 is rotated such that electrode assembly 24 is rotated to screw the helix into the target tissue through the cooperation of distal tip 26 and cavity 19. Pushing stylet 26 and guide catheter 21 are then removed from the patient leaving the implanted electrode assembly and lead body.

Figures 3A, 3B:
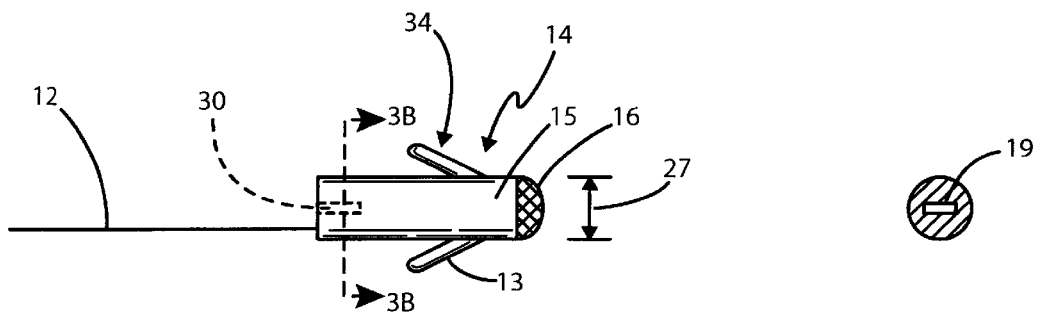
FIG. 3A illustrates a fragmentary side view of an alternative embodiment of a reduced diameter lead electrode assembly.
FIG. 3B illustrates a sectional view of the electrode assembly taken along line 3B—3B of FIG. 3A.

FIGS. 3A–E illustrate a further embodiment of the present invention, including a pacing electrode and an apparatus for implanting the electrode. FIG. 3A shows a unipolar electrode assembly 34 having an electrode housing 15, a tip electrode 16 and a lead body 12. Tip electrode 16 is configured within electrode housing 15 to confer a pacing stimulus on the heart when implanted in a patient. Tip electrode 16 is electrically coupled to a conductor (not shown) within lead body 12 at the leads distal end. At the proximal end of lead body 12, a lead connector pin such as shown in FIG. 1 is typically electrically coupled to the conductor.

Figure 3C:
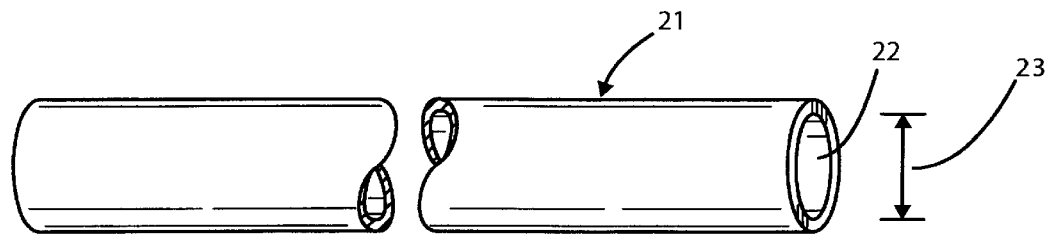
FIG. 3C illustrates a partial isometric view of a guide catheter for use during the implantation of the electrode assembly of FIG. 3A.
Figure 3D:
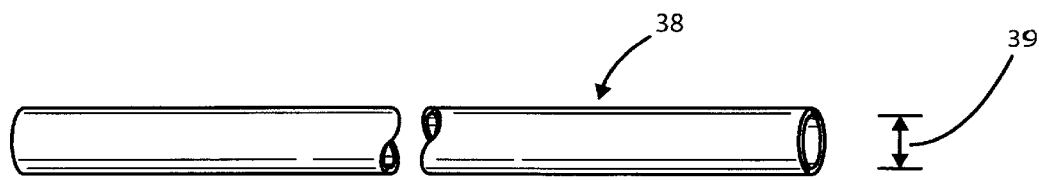
FIG. 3D illustrates a partial isometric view of an embodiment of a removal catheter for use during the implantation of the electrode assembly of FIG. 3A
Figure 3E:
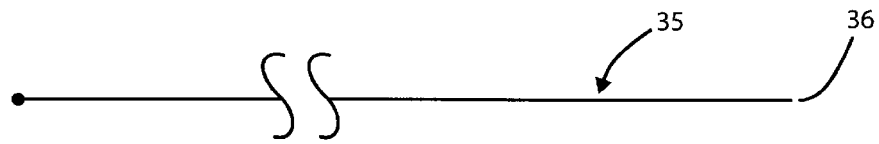
FIG. 3E illustrates a partial side view of a stylet for use during the implantation of the electrode assembly of FIG. 3A.

Pacing electrode assembly 34 (shown in FIG. 3A) is generally configured to advance through a guide catheter 21 (shown in FIG. 3C). The assembly is typically implanted at a target location in the right atrium or the right ventricle. To facilitate advancing through guide catheter 21, electrode assembly 34 is configured to have a smaller outside diameter 24 than the inside diameter 23 of lumen 22. Further, electrode assembly 34 is provided with a frictional cavity 30 at its proximal end. Frictional cavity 30 is configured to frictionally hold a distal tip 36 (shown in FIG. 3E) of a pushing stylet 35. Frictional cavity 30 frictionally holds distal tip 36 with sufficient force to prevent electrode assembly 34 from dislodging from stylet 35 during implantation. A removal catheter 38 (shown in FIG. 3C) can be provided to aid in removal of distal tip 36 from frictional cavity 30 after implantation. Removal catheter 38 typically has a lumen with an inside diameter 39 sufficient to receive pushing stylet 35 and lead body 12 in side-by-side relation. As shown in FIG. 3B, frictional cavity 30 has a rectangular shape designed to receive a rectangular shaped distal end 36 on stylet 35 for active fixation of electrode assembly 34. Alternatively, distal end 36 can have the variety of shapes as discussed for distal end 26 of FIG. 2D.

Guide catheter 21 may of the peel-away variety or may take other forms recognized by those skilled in the art. Guide catheter 21 is typically constructed of a biocompatible flexible material. Guide catheter 21 can include a radio-opaque coating or have a radio-opaque component included in its composition to facilitate visualization with fluoroscopy, magnetic resonance imaging, echocardiography, or by other methods known to those skilled in the art during implantation. Pushing stylet 35 is typically a biocompatible metal wire configured to push electrode assembly 34 through guide catheter 21. Pushing stylet 35 should be rigid enough to overcome the frictional and hydrostatic forces encountered as the electrode advances through guide catheter 21 to the target location in the heart. Distal tip 36 is typically round along its longitudinal axis, although, as mentioned above, when cooperating with frictional cavity 30 to actively fix an electrode, the shape will be such that a force can be conferred to electrode apparatus 34. Typically, the shape will be rectangular, triangular, square or any number of shapes known to those skilled in the art. Similarly, frictional cavity 30 is typically circular to receive distal tip 36, although its shape will cooperate with distal tip 36 when required for active fixation.

A method for implanting electrode assembly 34 is best understood with reference to FIGS. 3A–E. The method is described in the context of inserting an electrode into the right ventricle for exemplary purposes only. The distal end of guide catheter 21 is inserted into a vein of a patient using the Seldinger technique or other venipuncture techniques known to those skilled in the art. The distal end is guided through the veins and right atrium to the right ventricle and the tip is positioned adjacent the target location within the right ventricle. Typically, the distal end is guided to the target location with the assistance of fluoroscopy, magnetic resonance imaging, echocardiography, or by other methods known to those skilled in the art. Once positioned adjacent the target location, the distal end is held in position. Distal tip 36 of pushing stylet 35 is frictionally secured within frictional cavity 30. Electrode assembly 34 is then inserted into lumen 22 at the proximal end of guide catheter 21. As pushing stylet 35 is advanced into lumen 22, electrode assembly 34 is advanced toward the distal end of guide catheter 22. Upon reaching the target location, if electrode assembly 34 uses active fixation, the proximal end of pushing stylet 35 is rotated such that assembly 34 is rotated to secure the screw helix into the target location through the cooperation of distal tip 36 of the stylet and cavity 30. If electrode assembly 34 uses passive fixation, the tines are secured in the trabeculae.

Removal catheter 38 is then inserted into lumen 22 of guide catheter between pushing stylet 36 and guide catheter 21 at the proximal end. Removal catheter 38 is advanced toward the distal end of guide catheter 21 until the distal end of removal catheter 38 abuts the proximal end of electrode assembly 34. A dislodging force is then applied to removal catheter in the distal direction to counteract a proximally directed force applied by the user overcome frictional cavity's hold on distal end 36 of the pushing stylet. Once dislodged, pushing stylet 36, removal catheter 38 and guide catheter 21 are removed from the patient leaving the implanted electrode assembly and lead body.

FIGS. 4A–F illustrate yet another embodiment of the present invention, including a pacing electrode and an apparatus for implanting the electrode. FIG. 4A shows a bipolar electrode assembly 44 having an electrode housing 15, a tip electrode 16, a ring electrode 17 and a lead body 12. Tip electrode 16 and ring electrode 17 are electrically coupled as discussed above for the bipolar embodiment shown in FIG. 2A. The configurations of electrode assemblies are diverse and the application of the various configurations to the present invention will be evident to one skilled in the art.

Pacing electrode assembly 44 is generally configured to be removably secured in the distal end of a guide catheter 41 (shown in FIG. 4C). To facilitate being secured in guide catheter 21, electrode assembly 44 is provided with a flange 60 at its proximal end. Flange 60 has an outside flange diameter 61 and a flange length 62. Flange length 62 is the distance from the point that the electrode diameter 27 begins to increase to the electrode assembly's proximal end. Electrode assembly 44 can also be provided with a cavity 40 at its proximal end. Cavity 40 can be configured to cooperate with the shape of distal tip 46 (shown in FIG. 4E) of removal stylet 45 such that after electrode assembly 44 has been positioned at the target location distal tip 46 can confer a rotational force to fix a screw helix into the target location.

Guide catheter 41 is configured to removably secure electrode apparatus 44 within its distal end and to guide its distal end to a target position in the right atrium or the right ventricle. Guide catheter 41 may of the peel-away variety or take other forms recognized by those skilled in the art. Guide catheter 41 is typically constructed of a biocompatible flexible material. Guide catheter 41 can include radio-opaque marker bands, a radio-opaque coating or a radio-opaque component in its composition to facilitate visualization with fluoroscopy, magnetic resonance imaging, echocardiography, or by other methods known to those skilled in the art during implantation. Guide catheter 41 has a radially expandable distal end. The distal end defines a receiving cavity 65 to removably secure flange 60 of electrode apparatus 44. Receiving cavity 65 has an inside diameter 66 and a lumen orifice diameter 68 that correspond over a cavity length 67 to the dimensions of flange 60. In addition, receiving cavity 65 can include one or more radially extending slots 80 to facilitate the expansion of receiving cavity 65 for insertion and removal of electrode assembly 44. Typically, inside diameter 66 is slightly less than outside flange diameter 61 and lumen orifice diameter 68 is slightly less than electrode apparatus diameter 27 to compressionally hold electrode assembly 41 within receiving cavity 65. An internal stylet guide 78 can be provided within the lumen of guide catheter 41. Internal stylet guide 78 may be integrally molded into lumen 42 of guide catheter 41. Internal stylet guide 78 is generally configured to direct distal tip 46 of a stylet into cavity 40 of an electrode apparatus 44 secured within receiving cavity 65. In the embodiment shown in FIGS. 4C–D, internal stylet guide 78 presents an internal conical surface 79. Conical surface 79 guides the advancing distal tip 46 (shown in FIG. 4E) of a pushing stylet 45 through an internal orifice 70 into cavity 65. Internal orifice 70 is configured so that it is longitudinally coextensive with cavity 40 of electrode assembly 44 when electrode assembly 44 is secured within receiving cavity 65.

Removal stylet 45 is typically a biocompatible metal wire configured to push electrode assembly 44 from receiving cavity 45. Removal stylet 45 should be rigid enough to overcome the static, frictional, and elastic forces conferred on electrode apparatus 44 by receiving cavity 65. Distal tip 46 is typically round along its longitudinal axis, although, as mentioned above, the shape will be such that a rotational force can be conferred to electrode apparatus 44 when cooperating with cavity 19 to actively fix an electrode. Typically, the shape will be rectangular, triangular, square or any number of shapes known to those skilled in the art.

A method for implanting electrode assembly 44 is best understood with reference to FIGS. 4A–D. The method is described in the context of inserting an electrode into the right ventricle for exemplary purposes only. Reduced diameter lead body 12 is inserted through orifice 70 at the distal end of guide catheter 21. Electrode apparatus 44 is then secured in receiving cavity 65. The distal end of guide catheter 21 including electrode apparatus 44 is then inserted into a vein of a patient typically using the Seldinger technique or other venipuncture techniques known to those skilled in the art. The distal end is guided through the veins and right atrium to the right ventricle and is positioned at the target location. Typically, the distal end is guided to the target location with the assistance of fluoroscopy, magnetic resonance imaging, echocardiography, or by other methods known to those skilled in the art. If electrode 44 uses passive fixation, once positioned adjacent the target location, tines 13 are secured in the trabeculae. Distal tip 46 of removal stylet 45 is then inserted into lumen 42 at the guide catheter's proximal end. If electrode assembly 24 uses active fixation, either guide catheter 41 or removal stylet 45 may confer a rotational force to secure the screw helix (not shown) of electrode assembly 44. When guide catheter 41 is used, guide catheter 41 is rotated at the catheter's proximal end to secure the screw helix. When removal stylet 45 is used, the distal end 46 of removal stylet 45 is inserted through lumen 42 of guide catheter 41 at the catheter's proximal end. Removal stylet 45 is advanced toward the catheter's distal end and is directed into orifice 70 by stylet guide 78. Distal end 46 cooperates with cavity 40 to rotate the screw helix when the removal stylet's proximal end is rotated. In both passive and active fixation embodiments, removal stylet 45 is directed into orifice 70 by conical surface 79 to dislodge electrode assembly 44 from cavity 65. Removal stylet 45 is advanced until it either abuts a proximal end of electrode assembly 44 or, if present, is received by cavity 40. Removal stylet 44 then applies a force sufficient to dislodge electrode assembly 44 from cavity 65 to the proximal end of electrode assembly 44. The dislodging force is applied in a manner that minimizes tissue trauma. Once dislodged, removal stylet 45 and guide catheter 41 are removed from the patient leaving the implanted electrode assembly and lead body.

What is claimed is:

1. A method for implanting a lead, comprising:
    positioning a distal end of a guide catheter at a target location within a heart;
    inserting an electrode assembly of a predetermined diameter disposed at a distal end of a lead body whose diameter is less than the predetermined diameter in a proximal end of the guide catheter, the electrode assembly and not the lead body defining a stylet guide the stylet guide being a cavity at a proximal end of the electrode assembly, the stylet guide configured to guide and maintain a distal end of a pushing stylet on the proximal end of the electrode assembly;
    passing a pushing stylet through the guide catheter wherein the distal end of the pushing stylet abuts the proximal end of the electrode assembly pushing the electrode assembly to a target location through the catheter;
    securing the electrode at the target location; and
    withdrawing the stylet and the catheter from the heart.

2. A method, as in claim 1, wherein the cavity is configured to cooperate with the distal end of the pushing stylet to secure the electrode assembly.

3. A method, as in claim 1, wherein the guide catheter includes a radio-opaque coating.

4. A method, as in claim 1, wherein the positioning of the guide catheter is aided by at least one of fluoroscopy, magnetic resonance imaging and echocardiography.

5. A method for implanting a lead having a reduced diameter lead body affixed to an electrode assembly, comprising:
    positioning a distal end of a guide catheter at a target location within a heart;
    inserting a distal end of a pushing stylet into a cavity at a proximal end of the electrode assembly without passage through the lead body wherein the cavity is configured to frictionally engage a distal end of the pushing stylet;
    passing the pushing stylet and the electrode assembly through a proximal end the guide catheter and beyond until the electrode abuts the target location;
    fixing the electrode assembly at the target location;
    removing of the pushing stylet from the electrode assembly by inserting a removal catheter through the guide catheter and applying a force to the distal end of the electrode assembly to dislodge the pushing stylet from the cavity; and
    withdrawing the stylet and the catheter from the heart.

6. A method, as in claim 5, wherein the guide catheter includes a radio-opaque coating.

7. A method, as in claim 6, wherein the positioning of the guide catheter is aided by at least one of fluoroscopy, magnetic resonance imaging and echocardiography.

8. A lead, comprising:
    an electrode assembly defining a frustoconical flange at a proximal end of the electrode assembly, the flange configured to secure the proximal end within a resilient, frustoconical receiving cavity disposed at a distal end of a guide catheter; and
    a lead body of reduced diameter compared with the electrode assembly, the reduced diameter lead body electrically coupled to the electrode assembly.

9. A lead, as in claim 8, wherein the reduced diameter lead body comprises a cable conductor and an insulator.

10. A lead, as in claim 8, wherein the reduced diameter lead body comprises a coil conductor and an insulator.

11. A lead, as in claim 8, wherein the electrode assembly is a passive fixation electrode assembly.

12. A lead, as in claim 11, wherein the electrode assembly is provided with at least one tine.

13. A lead, as in claim 8, wherein the electrode assembly is an active fixation electrode assembly.

14. A lead, as in claim 13, wherein the electrode assembly is provided with a screw helix.

* * * * *

UNITED STATES PATENT AND TRADEMARK OFFICE
CERTIFICATE OF CORRECTION

PATENT NO.     : 6,370,434 B1
DATED          : April 9, 2002
INVENTOR(S)    : Yongxing Zhang and James O.Gilkerson It is certified that error appears in the above-identified patent and that said Letters Patent is hereby corrected as shown below:

<u>Column 12,</u>
Beginning at line 62, please add the following claim:

13. A method, as in Claim 8, wherein the distal end of the guide catheter is provided with at least one radially extending slot to facilitate the detaching of the electrode assembly.

Signed and Sealed this

Thirteenth Day of August, 2002

*Attest:*

JAMES E. ROGAN
*Director of the United States Patent and Trademark Office*

*Attesting Officer*